(12) United States Patent
Ma et al.

(10) Patent No.: US 8,979,762 B2
(45) Date of Patent: Mar. 17, 2015

(54) METHOD OF DETERMINING BODY PARAMETERS DURING EXERCISE

(75) Inventors: Chor Tin Ma, Hong Kong (CN); Kai Kin Chan, Hong Kong (CN); Ming Yip Wong, Hong Kong (CN); Kai Wai Yeung, Hong Kong (CN); Fo Chau, Hong Kong (CN)

(73) Assignee: Well Being Digital Limited, Hong Kong (HK)

( * ) Notice: Subject to any disclaimer, the term of this patent is extended or adjusted under 35 U.S.C. 154(b) by 1134 days.

(21) Appl. No.: 12/195,502

(22) Filed: Aug. 21, 2008

(65) Prior Publication Data

US 2009/0177097 A1 Jul. 9, 2009

Related U.S. Application Data

(60) Provisional application No. 61/006,321, filed on Jan. 7, 2008.

(51) Int. Cl.
| | | |
|---|---|---|
| *A61B 5/02* | (2006.01) | |
| *A61B 5/04* | (2006.01) | |
| *A61B 5/024* | (2006.01) | |
| *A61B 5/00* | (2006.01) | |
| *A63B 24/00* | (2006.01) | |
| *A63B 71/06* | (2006.01) | |

(52) U.S. Cl.
CPC ......... *A61B 5/02433* (2013.01); *A61B 5/02438* (2013.01); *A61B 5/6817* (2013.01); *A61B 5/6824* (2013.01); *A63B 24/0062* (2013.01); *A63B 71/0686* (2013.01); *A63B 2230/06* (2013.01)
USPC ............................ 600/500; 600/509; 600/513

(58) Field of Classification Search
None
See application file for complete search history.

(56) References Cited

U.S. PATENT DOCUMENTS

| | | | |
|---|---|---|---|
| 4,301,808 A | | 11/1981 | Taus |
| 4,938,228 A | * | 7/1990 | Righter et al. ................ 600/503 |
| 5,314,389 A | | 5/1994 | Dotan |
| 6,080,110 A | | 6/2000 | Thorgersen |
| 6,808,473 B2 | | 10/2004 | Hisano et al. |
| 7,164,938 B2 | | 1/2007 | Geddes et al. |
| 7,175,601 B2 | | 2/2007 | Verjus et al. |
| 7,209,775 B2 | | 4/2007 | Bae et al. |
| 2003/0065269 A1 | * | 4/2003 | Vetter et al. .................... 600/503 |
| 2005/0113650 A1 | * | 5/2005 | Pacione et al. ................ 600/300 |

OTHER PUBLICATIONS

M. R. Neuman, et al., *Motion Artifact in Pulse Oximetry*, 2 pages, Annual Int'l., Conference of the IEEE Engineering in Medicine and Biology Society, vol. 12, No. 5, 1990, 2007-2008.

* cited by examiner

*Primary Examiner* — Benjamin P Blumel
(74) *Attorney, Agent, or Firm* — William J. Sapone; Ware Fressola Maguire & Barber LLP

(57) ABSTRACT

A noninvasive light sensor for detecting heart beat signals has a circular support member engageable circumferentially with a body part of a person. Light emitters and light detectors are located around a circumference of the circular support member for respectively emitting light signals into different areas of tissue surrounding the body part, and detecting reflected light signals from the different areas of tissue surrounding the body part.

8 Claims, 9 Drawing Sheets

METHOD OF DETERMINING BODY PARAMETERS DURING EXERCISE

BACKGROUND TO THE INVENTION

1. Field of the Invention

The current invention relates to an exercise device for monitoring body parameters of a wearer during exercise. The invention also relates to sensor for determining sensor signals from which body parameters can be derived and to a method of determining body parameters during exercise.

2. Background Information

To achieve fitness goals it is necessary to exercise in the right intensity. Heart rate is one of the most accurate measurements of the intensity or exertion level of an exercise workout. The fitness of the heart is the key to aerobic endurance. Aerobic endurance is extremely important for both general fitness training and professional athletes. Heart monitors are one of the most effective aids for tracking and developing the progress on the path to increased aerobic endurance. For example, to loss weight and burn fat, it is desirable to exercise at 60-70% of one's maximum heart rate. To improve cardiovascular fitness, it is more suitable to exercise at 70-80% of one's maximum heart rate. Exercise at the wrong intensity will just waste the effort or may even harm the body.

Heart rate can easily be checked by checking the pulses at the wrist manually for, say, 15 seconds during exercise and calculate beats per minute. However, stopping during exercise to count pulse is not only inconvenient, but also disrupts both the workout and the heart rate. This method also introduces pressure to the carotid artery which slows down the pulse. Electronic heart monitors are an effective way to track and record heart rate over the course of an entire workout. They not only provide a complete record of the heart rate for the duration of your workout, but they are also more accurate than manual methods, and can provide other information such as body temperature, SpO2 (Oxyhemoglobin saturation by pulse oximetry) are also important information to determine condition of the body.

For professional athletes, cardiovascular fitness is the most significant factor in speed. Measuring the work-rate of the heart is one of the most accurate methods of determining how much benefit an athlete derives from a workout. A heart rate monitor can also help to avoid stressing the body too much. They are a useful tool for maximize the efficiency of the training while minimizing the opportunity for injury. Heart rate monitors also enable professional athletes to exercise below a certain ceiling, i.e. avoid depleting the body's glycogen stores and ensuring that the body has the energy to perform intense workouts with vigor. For general fitness training, a heart rate monitor can function as a coach guiding the user when he or she can handle more and work harder.

Most popular heart rate monitors use ECG type chest belt with a wireless link to sports watch. The heartbeat is detected by sensing the ECG signal from the chest belt and a pulse is sent to the sports watch via wireless connection. This type of heart rate monitor is accurate and reliable, but has the disadvantage that it is not comfortable for the user to wear a plastic belt on the chest during exercise. The belt will also become very dirty after use. Another method of detecting heartbeat is to use IR LED and IR sensor through the ear lobe or finger tip. This type of detector has the intrinsic problem of motion artifact and they are simply not reliable during exercise.

There are many devices that can measure body parameters of a person. For example, by using an infrared ear thermometer, clinical thermometer, the user could get his body temperature and by using pulse oximeter the user could get his heartbeat and the amount of oxygen attached to the hemoglobin. However, none of these devices is suitable for continuous monitoring of the body parameter when the user is doing exercise. The thermometer, for example, is not suitable for use in motion. For finger pulse oximeter, study suggested the motion will result in blood volume changes that invalidate its measurement [ref—"Motion Artifact in Pulse Oximetry", M. R. Neuman and N. Wang, Annual International Conference of the IEEE Engineering in Medicine and Biology Society, Vol. 12 No. 5, 1990].

FIG. 1 is a schematic illustration is a typical finger type pulse oximeter implementation. Measuring heartbeat rate and SpO2 (blood oxygenation) is based on the absorption of red and infrared light. The technology is very sensitive to motion and hence is generally not suitable for use in personal exercise monitors. A few mechanical designs attempt to improve motion tolerance and enable the measurement to be used later in signal processing such that the heart rate in addition to SpO2 can be derived when the wearer is in motion. The device comprises two light sources, typically using LEDs of known wavelength. The wavelengths of the two light sources are 880-920 nm (Infrared or IR) and 660 nm (Red) respectively. To obtain heart rate (HR) only the IR light source is needed. To calculate blood oxygen levels (pulse oximetry) both the Red and the IR LED's would need to be used. In either case a photo detector is used to sense the light that has been transmitted or reflected into the skin or application sight. This transmission of light into an area of the body that is carrying blood and reflected back to the photo detector will be effected by the pulsiltile flow caused by each heartbeat. This slight change in light intensity is detected and extracted to create a waveform commonly known as a plethysmograph. This waveform or the actual detection of the pulsiltile flow can be converted into heart rate in the absent of motion. To calculate pulse oximetry the IR and the red light emissions are separately analyzed and then used in an empirical calculation to generate a predetermined blood oxygen level. The calibration and empirical calculation can be found in many literatures.

FIG. 2 shows an example of noise induced by motion in an IR LED and IR heartbeat/SpO2 sensor. This noise signal may be of similar or even larger amplitude than the heartbeat signal and they are, in normal situation, in the same frequency band of the heartbeat signal (1-3 Hz). There is no easy method to extract the heartbeat signal from the mixture of the motion signal and heartbeat signal.

SUMMARY OF THE INVENTION

Accordingly, is an object of the present invention to provide an exercise device for determining the body parameters of a wearer during exercise. This particular object of the present invention to provide a sensor and method of determining heartbeat from a sensor signal that overcome or at least ameliorates problems with known devices.

A noninvasive light sensor for detecting heart beat signals has a circular support member engageable circumferentially with a body part of a person. A plurality of light emitters and light detectors are located about a circumference of the circular support member for respectively emitting light signals into different areas of tissue surrounding the body part, and receiving reflected light signals from the different areas of tissue surrounding the body part. In preferred embodiments the support member is one of a ear bud insertable within an ear canal or a band locatable about a wrist or arm.

The light emitters and light detectors may comprises both red and infra-red light emitters and detectors. In preferred embodiments there are three light emitters located 120 degrees apart about the circumference of the support member and three light detectors located 120 degrees apart about the circumference of the support member. The light emitters and light detectors are preferably located in pairs consisting of one of the emitters and one of the detectors.

Further aspects of the invention will become apparent from the following description.

BRIEF DESCRIPTION OF THE DRAWINGS

An exemplary form of the present invention will now be described by way of example only and with reference to the accompanying drawings, in which.

DESCRIPTION OF THE EXEMPLARY EMBODIMENTS

Aspects of the invention will now be illustrated as practiced in a first embodiment of a personal exercise device comprising an earphone sensor for listening to audio files and also for detecting body parameters; such as heartbeat, SpO2 and temperature; during exercise, a signal processing means for resolving sensor information into heartbeat and other body parameters and a workout assistance means for providing feedback of body parameters, exercise instructions and entertainment functions such as, but not limited to, music, video, game, e-book, photo, etc. However, this is not intended to limit the scope of functionality or use of the invention. In a most basic embodiment of the invention the exercise device comprises simply an earpiece sensor and signal processing means for detecting heartbeat for feedback to the user or transmission to another device such as an exercise machine or exercise monitoring equipment. The earphones of the invention include several mechanical design characteristics that ameliorate movement inaccuracies inherent in ear sensors known hitherto. It is not essential to the invention that all such preferred mechanical design characteristics be included in all embodiments of the invention.

Figure 1:
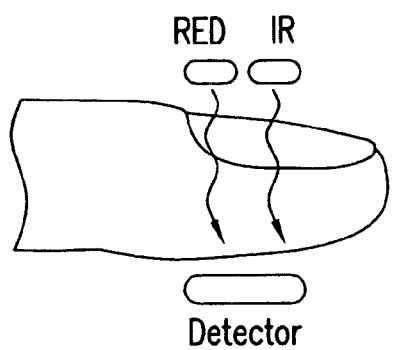
FIG. 1 is a schematic illustration of prior art operation of a heartbeat sensor/pulse oximeter.
Figure 2:
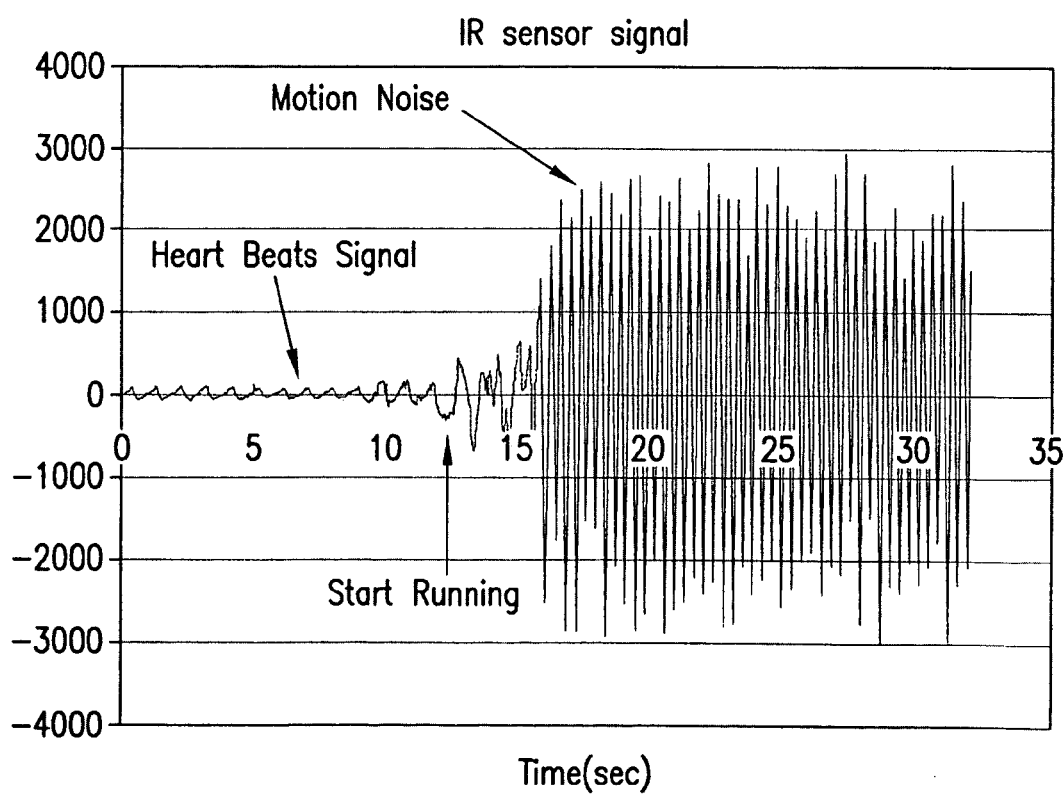
FIG. 2 is a graphical illustration of the heartbeat signal with motion noise for a prior art earphone sensor.
Figure 3:
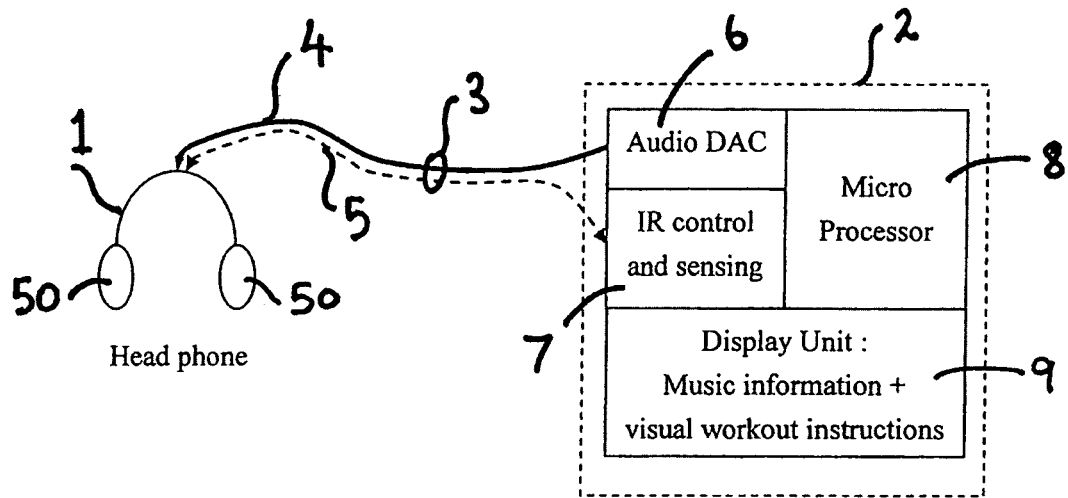
FIG. 3 is a schematic illustration of a first embodiment of a personal exercise device according to the invention having an earphone type sensor.

FIG. 3 shows the block diagram of a personal exercise device. A pair of earphones 1 that can be worn by the user is connected to a portable base unit 2 by a cable 3 having conductor means 4, 5 for carrying both audio signals and body parameter sensor signals. The portable base unit 2 has a microprocessor 8, audio module 6 for providing audio signals to the earphones, a sensor module 7 for communicating with the earphone sensors and a user interface/display module 9 for interaction with the user. In one exercise mode the exercise device determines heartbeat of the user and then controls the playback of audio content in accordance with changes in the heartbeat. The heartbeat is also recorded for future reference and for comparing against targeted training level, etc. The earphones 1 may also include an IR thermometer or small thermistor embedded in the earphones 50 for determining body temperature. The bases unit and or earphones 50 may also include an accelerometer/G-sensor for detecting steps from running or walking motion. The earphones may also include a microphone for picking up ambient sound signal and the user could enable or disable or adjusting the ratio of the mixing of ambient sound with content playing back at will. This is necessary because of the mechanical structure for the ear buds blocks a significant part of ambient sound from reaching the user.

Figure 4:
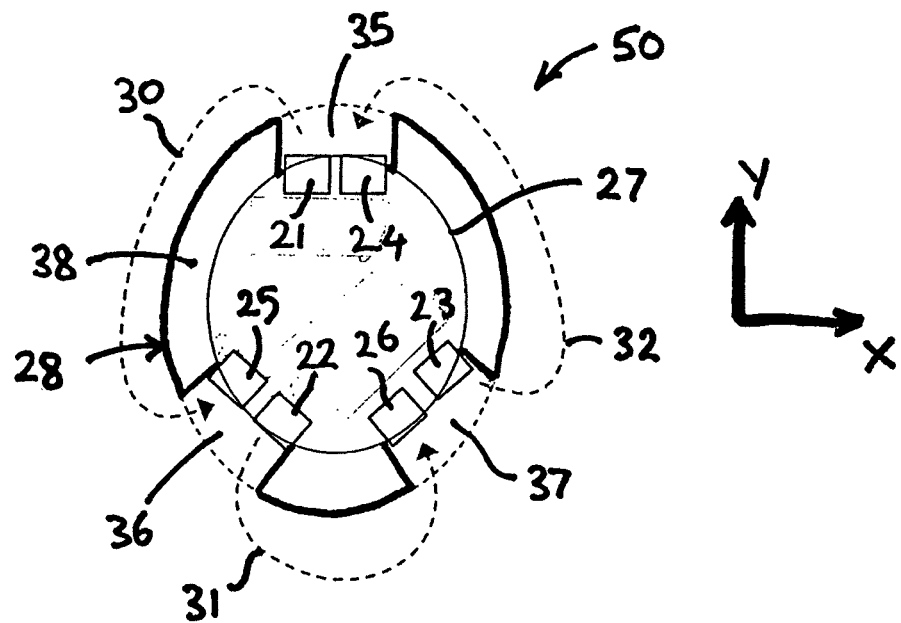
FIG. 4 is a schematic illustration of the earphone sensor arrangement for device of FIG. 3.
Figure 5:
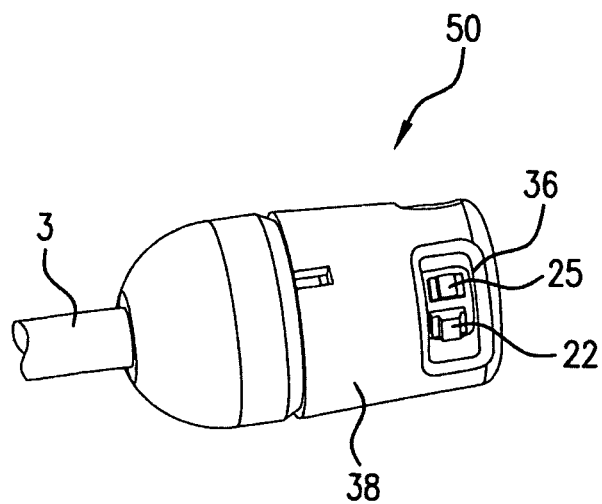
FIG. 5 is a perspective illustration of an ear bud of the earphone sensor.
Figure 6:
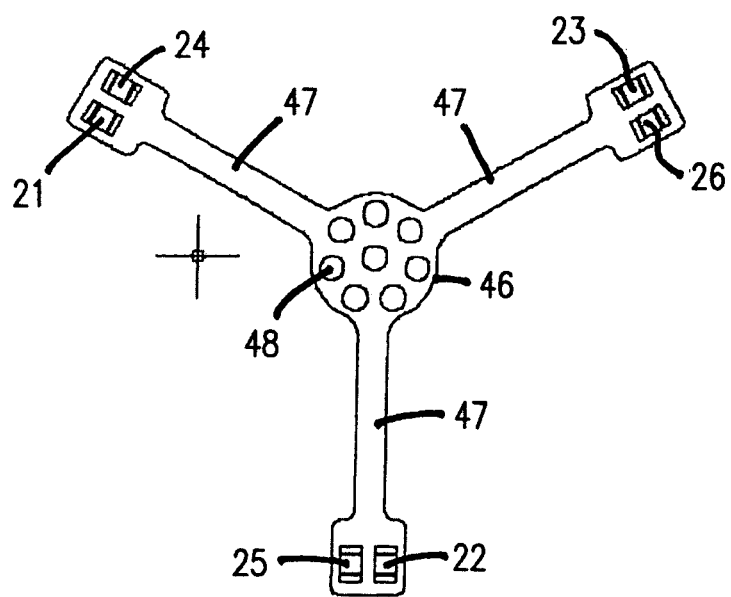
FIG. 6 is a schematic illustration of a flexible printed circuit (FPC) for locating and connection of sensors within the ear bud.

The earphone mechanical design is illustrated in FIGS. 4 through 10. FIG. 4 schematically illustrates the sensor arrangement of the earphones. Signal emitter 21, 22, 23 and detector 24, 24, 26 devices are located around the circumferential periphery 27 of the earphone. The emitter and detector devices may be either Red or Infrared (IR) or both for detecting heartbeat and optionally SpO2. The ear piece is of a type commonly known as an ear bud 50 which has a substantially cylindrical shape for insertion within the outer ear canal of the wearer. In the preferred embodiment the emitters and detectors are grouped in pairs 21-24, 22-25, 23-26 located 120 degrees apart about the circumferential periphery 27 of the ear bud 50. The dashed lines 30, 31, 32 show the path of the IR signals through the soft tissue surrounding the internal wall of the ear canal. A first signal 31 from emitter 21 is detected by detector 25, a second signal 32 from emitter 22 is detected by detector 26 and a third signal 33 from emitter 23 is detected by detector 24. The main signal noise is due to radial motion of the ear bud 50 in the x, y plane within the ear cannel because these movement changes the distance between the sensor and the ear canal wall, which affects the transmitted and receive signal. By using the physical construction where the IR sensors are installed in several circular symmetric locations the effect due to motion in the x, y plane can be approximated as a linear effect on the amplitude of the received signal. It should be noted that the invention has the optimal performance when the IR sensors are installed symmetrically but this should not be a limitation of the invention.

Some of the signal emitted from the emitters 21, 22, 23 will be reflected from the skin surface of the ear canal. The amount of the IR signals 31, 32, 33 that is reflected from the skin also varies substantially with the aforementioned x, y plane movement of the ear bud 50 within the ear canal. The reflected light is detected by the detectors and must be allowed for in later processing to determine heartbeat and other body parameters from the detected signals. The amount of referred light that is detected by the detectors can be ameliorated by locating the emitters and detectors within recess channels 35, 36, 37 below the outer peripheral surface 28 of the ear bud 50. The recess channels 35, 36, 37 can comprise air or optical glass mediums and form a narrow angle wave guide for IR signals emitted from the emitters or entering the detectors. These wave guide channels 35, 36, 37 produces a narrow angle beam to direct the light in such a way to allow the maximum amount signal by increasing the signal path of the light up and into deeper tissue before the light reflects and is captured by the detector. They also limiting large fluctuation in DC single picked up by detectors.

The outer part 38 of the ear bud 50 consists of a soft over-molding made of resiliently deformable memory foam or silicone rubber that dampens the effects of motion. The foam is compressed when the ear bud 50 is inserted into the ear canal and expands to hold the bud 50 firmly in the ear canal to ameliorate relative motion between the emitters and detectors and the ear canal wall during exercise movement. One possible optional feature is to make outer piece 38 removable and interchangeable for varying the size and shape to fit a wide variety of users having different size ear canals. The properties (elasticity, softness as known as durometer, memory or rebound rate) of this soft over-molding 38 are chosen to maximizing the damping effects.

The depth placement of the emitters and detectors inside the ear is also important, but not essential, to reducing the effects of motion introduced within the ear during exercise. The emitters and detector are placed at the end of the inner part of the ear bud 50 which is further into the ear canal to help reduce the effects of motion. This placement helps reduce the vibration as the inner ear part is more firmly attached to the bone and muscle (non-soft tissue) which does not move as much during exercise.

Figure 7:
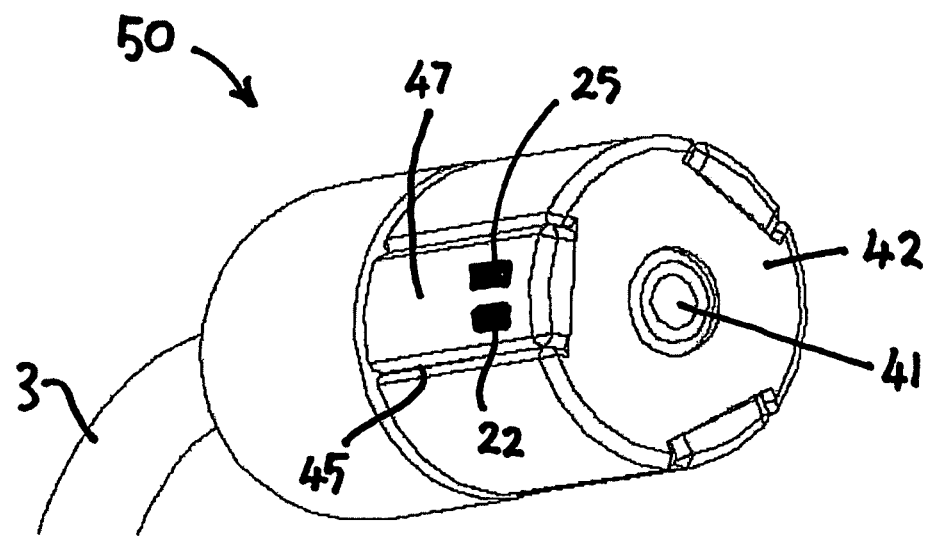
FIG. 7 is a perspective illustration of the ear bud without a rubber over-molding.
Figure 8:
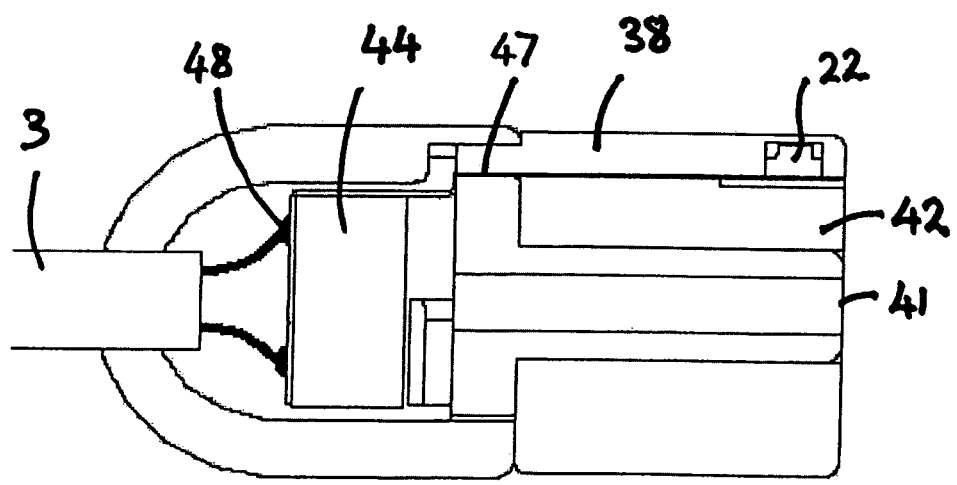
FIG. 8 is a section illustration of the ear bud.

A first arrangement of an ear bud 50 is illustrated in FIGS. 5 through 8. The interchangeable resilient outer part 38 is sized to fit within the ear canal of a person. FIG. 7 illustrates the core parts of the ear bud 50 with the resilient outer part 38 removed. The structure consists of a speaker 44, a hollow inner core 41 for sound conduction from the speaker in to the ear, an resilient inner foam structure 42 for softness and flexibility, FPC 43 or thin wirings for connection to emitter and detectors and a rubber over-molding 38 for increase comfort and protection of sensors. The resilient inner foam 42 may be compressed during insertion of the bud 50 into the ear to provide further support in the ear canal.

The FPC 43 comprises a hub 46 having three 120 degree radially extending arms 47. The emitter and detector pairs 21-24, 22-25, 23-26 are located at the distal ends of the FPC 43 and are encapsulated with epoxy. The encapsulation provides a round-top to avoid injury to the user when wearing the device and at the same time prevents the emitters and receivers from damage. An alternative approach is to use sensors with suitable packaging. The FPC arms 47 are made of a flexible material so that sensors follow the foam 42 when squeezed into the ear canal. Flexible wiring tracks are located along the radial arms 47 connecting the emitters and detectors to solder bonding pads 48 on the hub 46. In one embodiment the FPC and arms is formed as a flex circuit. The hub 46 is located centrally within the back of the ear bud 50 and the radial arms brought forward within slots 45 on the surface of foam 42. The depth of the slots 45 is designed to allow the sensors to be slightly above the foam surface. The foam 42 is then covered with the rubber over-molding 38 for increase comfort and protection of sensors.

Figure 9:
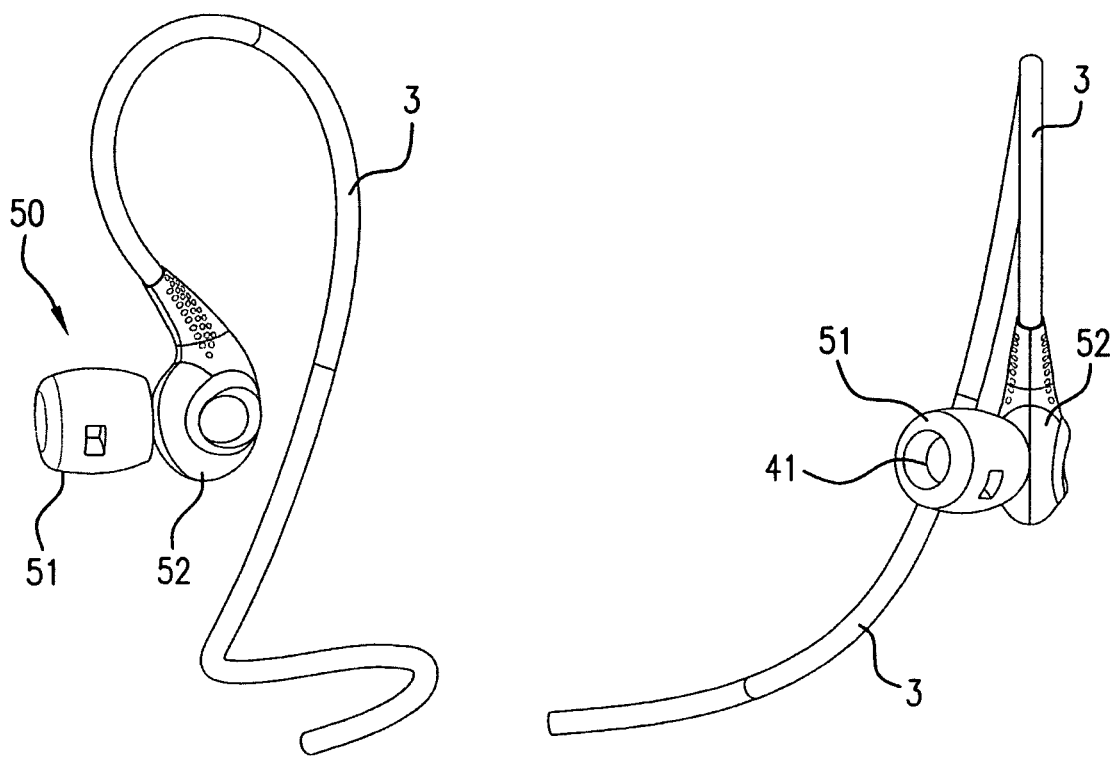
FIG. 9 is a perspective illustration of an alternative ear bud type earphone sensor.
Figure 10:
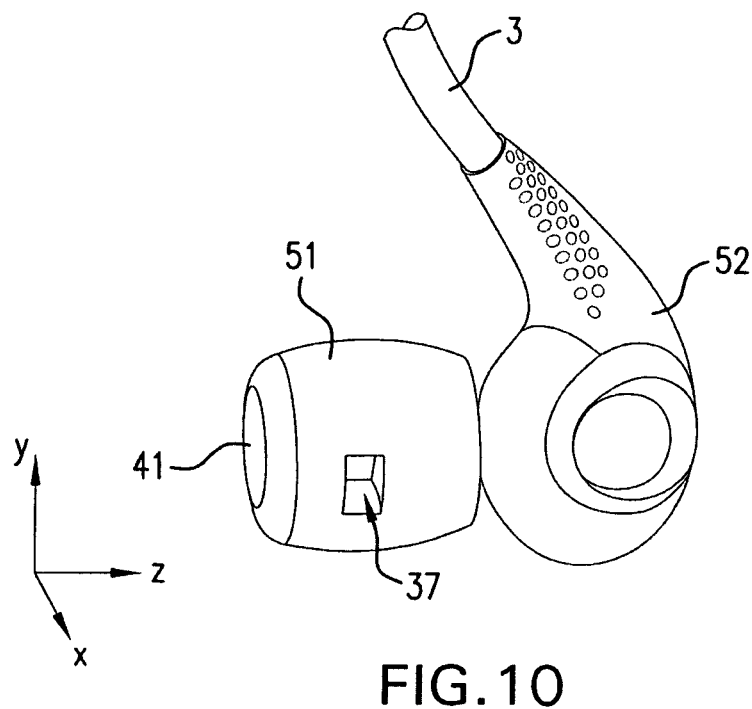
FIG. 10 is a perspective illustration of a bud and behind-the-ear parts of the alternative ear bud.

FIGS. 9 and 10 illustrate an alternative arrangement of an ear bud 50 in a behind-the-ear design. The cord 3 to each bud 50, hangs around the back of the ear to also help in securing an in ear portion 51 into the ear canal and thus reducing motion introduced into the signal by exercise movement. Another feature of this design is to have the cable 3 enter at the back or bottom of the behind the ear portion. This cable placement design will reduce the motion effects that can be produced by the pulling forces of the cable during movement. Since the cable 3 can exert a force on the ear piece the reduction of its size and weight is achieved by locating some of the electronics or circuitry into a behind an ear portion 52 of the earphone. This feature reduces the number of wires and thus thickness and weight of the cable 3. There are many wires needed to drive and capture the signal from the emitters and detector as well as the wires for the audio speakers and the temperature sensor. The circuit design has a communication method between the main unit 2 and the behind the ear portion 52 circuitry.

Figure 11:
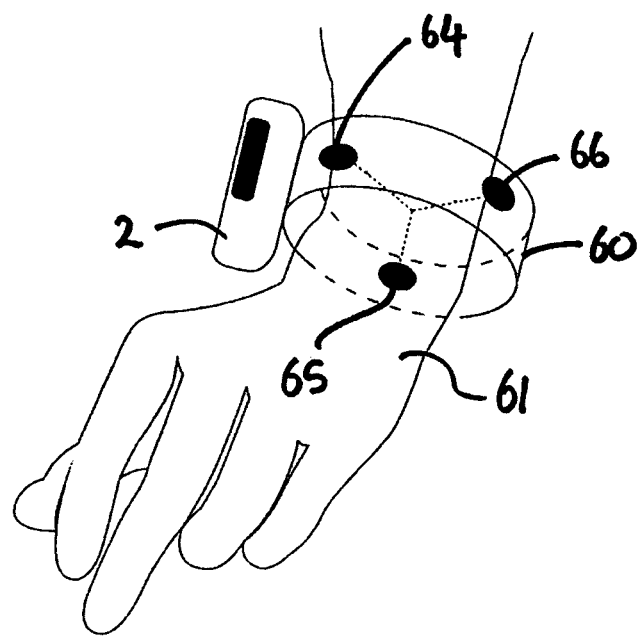
FIG. 11 is a schematic illustration of a second embodiment of a personal exercise device according to the invention having a arm band type sensor.
Figure 12:
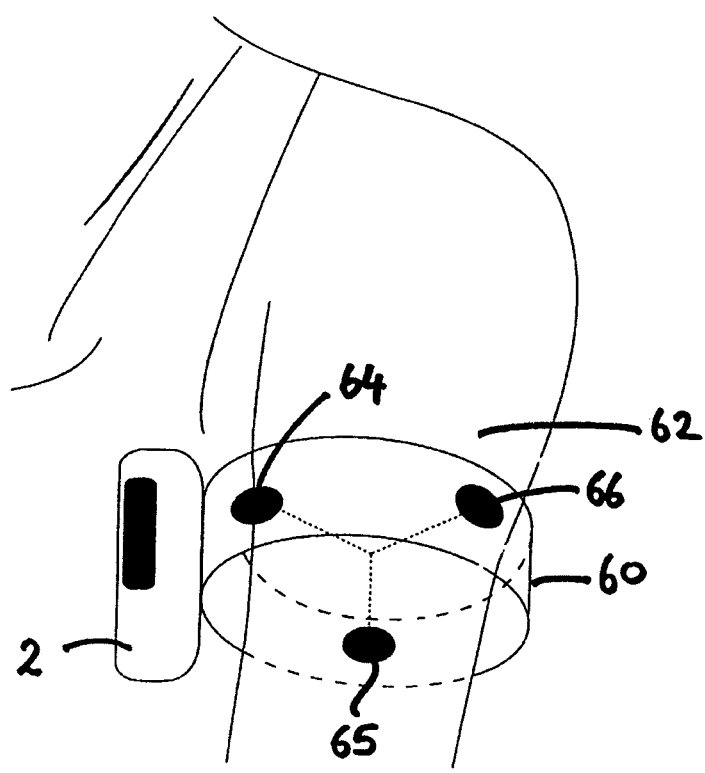
FIG. 12 is a second schematic illustration of the personal exercise device having a arm band type sensor.

FIGS. 11 and 12 illustrate a second embodiment of an exercise device according to the invention employing an armband type sensor. In the first embodiment the sensor was a circular ear bud for location within an ear canal, with the emitters and detectors located in pairs 120 degrees apart around the outer circumference of the bud for obtaining signals from the tissue surrounding the ear canal. In the armband embodiment an annular band 60 is provided which locates about the wrist 61 or upper arm 62 of the user. Emitters and detectors are provided in three pairs 64, 65, 66 at locations 120 degrees apart around the inner circumference of the band 60. The emitters and detectors are of the same type as in the ear bud, however the emitters and detectors are located on the inner circumference of the band 60 so as to be pressed up against the skin of the wrist 61 or arm 62 when the band 60 is worn. The sensor signal path is through the tissue of the wrist 61 or arm 62. The band 60 is made of a resilient material so as to fit snugly about the wrist 61 or arm 62 of the wearer and maintain the emitter and detector pairs 64, 65, 66 in position with the arm tissue. The band 60 may be a stand alone band or, as illustrated in FIGS. 11 and 12, may be a support strap for wearing the portable base unit 2 on the wrist 61 or upper arm 62 of the users. The arm-band embodiment may be preferable to those who run or cycle in busy traffic areas and prefer not to impair their hearing with earphones for safety reasons. The embodiment shown in FIG. 11 may be, for example, a wrist watch wherein the base unit only provides visual feedback. However, in some embodiments the base unit 2 may also have an ear phone output jack for connection of a standard pair of earphones for listening to music and audio feedback from the portable exercise device if so desired.

Figure 13:
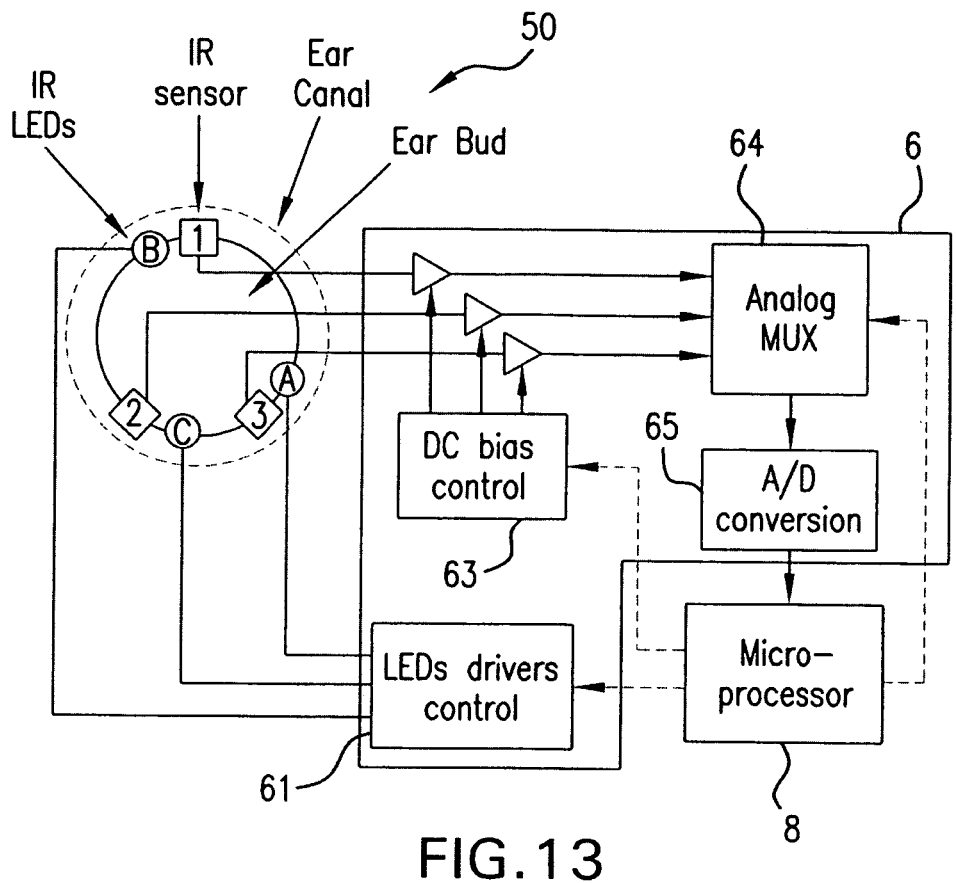
FIG. 13 is a schematic illustration of the sensor control and processing means of the exercise device.

The head phones 1 and arm bands 60 of embodiments of the invention use multiple pairs of emitters and detectors at symmetrical locations to aid the removal or minimization of the additive noise introduced in to the detected sensor signals by exercise motion of the wearer. The microprocessor 8 of the main unit 2 receives the detected sensor signals and analyses them to detect the wearer's heartbeat and other body parameters, such as SpO2. FIG. 13 is a schematic block diagram of the sensor control and processing means. A LED driver control is used to send driving signals to the LED emitters 21, 22, 23. The detected signals from detectors 24, 25, 26 are amplified by op-amps 62 with DC bias control 63. The amplified analog signals go through a multiplexer 64 and an analog-to-digital (A/D) converter 65 for input to the Microprocessor 8.

The signals are analyzed in Microprocessor 8 to detect the wearer's heartbeat and other body parameters.

The detected signals 31, 32, 33 are modeled as follows:

$$m_1(t)=L_1 I_{01}(t)(1+\gamma_1 hb(t))(1+N_{s1}(t)+N_{f1}(t)+z_1(t)) \quad (1)$$

$$m_2(t)=L_2 I_{02}(t)(1+\gamma_2 hb(t))(1+N_{s2}(t)+N_{f2}(t)+z_2(t)), \text{ and} \quad (2)$$

$$m_3(t)=L_3 I_{03}(t)(1+\gamma_3 hb(t))(1+N_{s3}(t)+N_{f3}(t)+z_3(t)) \quad (3)$$

Where:
- $m_1(t)$, $m_2(t)$, $m_3(t)$ are the signal received at the 3 detectors respectively
- $I_{01}(t)$, $I_{02}(t)$, $I_{03}(t)$ are the transmitted signal to the IR LED emitters respectively
- $L_1$, $L_2$, $L_3$ are constant gain of each IR sensors
- $hb(t)$ is the heartbeat signal
- $\gamma_1$, $\gamma_2$, $\gamma_3$ are coupling coefficients of the heartbeat signal $hb(t)$
- $N_{s1}(t)$, $N_{s2}(t)$, $N_{s3}(t)$ are slow varying noise in the detected signals
- $N_{f1}(t)$, $N_{f2}(t)$, $N_{f3}(t)$ are typical additive thermal noise in the detected signals, and
- $z_1(t)$, $z_2(t)$, $z_3(t)$ are noise signals due to motion.

Figure 14:
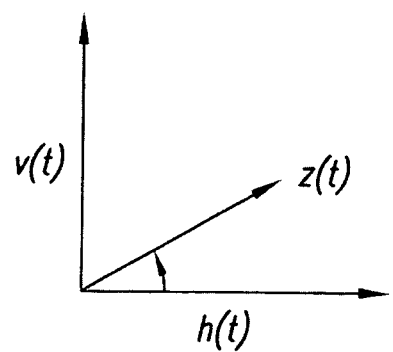
FIG. 14 is a graphical illustration of the signal detected during exercise.

This model is based on the assumption that the motion signals $z_1(t)$, $z_2(t)$, $z_3(t)$ are in the same plane as the circular plane formed by the 3 sensors (the x-y plane) and they can be decomposed to 2 orthogonal components $h(t)$ and $v(t)$ as shown in FIG. 14. Mathematically this is $z_k(t)=\epsilon_k(h(t)\cos(\theta_k)+v(t)\sin(\theta_k))$, where $h(t)$, $v(t)$ are the motion signal being projected to horizontal and vertical directions and the direction of sensor k is $\theta_k$ from the horizontal direction and $\epsilon_k$ are coupling coefficients for the motion signal to the sensors. For the three detectors 120 degrees apart $\theta_k$ is 90, 210 and 330 degrees.

We can make the assuming that both $\gamma_k$, $\epsilon_k$ are much smaller than 1 and we can represent the received signal as DC and AC components ($m_{ack}(t)$, $m_{dck}(t)$). By calculating the signal AC amplitude when there is no motion, we can normalize the 3 channels gain. Equations (1), (2), (3) can be approximated as:

$$m_{ac1}(t)=hb(t)+N'_{s1}(t)+N'_{f1}(t)+z_1'(t) \quad (4)$$

$$m_{ac2}(t)=hb(t)+N'_{s2}(t)+N'_{f2}(t)+z_2'(t) \quad (5)$$

$$m_{ac3}(t)=hb(t)+N'_{s3}(t)+N'_{f3}(t)+z_3'(t) \quad (6)$$

where $N'_{sk}(t)$, $N'_{fk}(t)$, $z_k'(t)$ are scaled versions of the original signals.

The signal due to heartbeat should have similar effect on the three signals 31, 32, 33 and should be in phase in each signal and differ only by a scaling factor. The sensors are placed evenly in a circle and so the effect of motion in x-y plane should be different for the 3 symmetrically located sensors. When there is no motion, or a very small amount of motion, the maximum signal to noise ratio (SNR) of the heartbeat signal can be obtained by adding up the three AC component input signal, i.e. $y(t)=m_{ac1}(t)+m_{ac2}(t)+m_{ac3}(t)$.

When there is exercise motion the noise signals $z_1'(t)$, $z_2'(t)$, $z_3'(t)$ become dominated in the received signals 31, 32, 33. We can solve this problem by finding the column vector $\hat{w}=[w_1\ w_2\ w_3]^T$ such that $\hat{y}=\hat{w}^T M$ where $$M = \begin{bmatrix} m_{ac1}[0] & m_{ac1}[1] & \ldots & \ldots & m_{ac1}[K-1] \\ m_{ac2}[0] & m_{ac2}[1] & \ldots & \ldots & m_{ac2}[K-1] \\ m_{ac3}[0] & m_{ac3}[1] & \ldots & \ldots & m_{ac3}[K-1] \end{bmatrix} \text{ and}$$

$$\hat{y} = [y[0]\ y[1]\ \ldots\ y[K-1]]$$

and $\hat{y}$ is a linear combination of input signal which maximize:

$$\frac{\hat{w}^T \hat{s} \hat{s}^T \hat{w}}{\hat{w}^T \mathfrak{R}_{mm} \hat{w}}$$

where $\mathfrak{R}_{mm}$ is the cross correlation matrix of the 3 signals from motion.

$\hat{s}=[s_1\ s_2\ s_3]^T$ is the corresponding gain of the heartbeat signal, in this case where all the 3 input channels are normalized.

$\hat{s}=[1\ 1\ 1]^T$ and $\mathfrak{R}_{mm}=MM^T-\sigma^2 \hat{s}\hat{s}^T$ where $\sigma^2$ is the variance of the heartbeat signal.

Since $\mathfrak{R}_{mm}$ is positive definite, we can write $$\mathfrak{R}_{mm} = R^{\frac{1}{2}} \cdot R^{\frac{1}{2}}$$

and we write $$\hat{u} = R^{\frac{1}{2}} \hat{w}$$

$$\hat{w} = R^{-\frac{1}{2}} \hat{u}$$

The problem becomes:

$$\max_{\|\hat{u}\|=1} \hat{u}^T R^{-\frac{1}{2}} \hat{s} \cdot \hat{s}^T R^{-\frac{1}{2}} \hat{u}$$

or $$\max_{\|\hat{u}\|=1} (\hat{u}^T R^{-\frac{1}{2}} \hat{s})^2$$

The expression is maximum when:

$$\hat{u} = R^{-\frac{1}{2}} \hat{s}$$

$$\therefore \hat{w} = R^{-\frac{1}{2}} (R^{-\frac{1}{2}} \hat{s}) = \mathfrak{R}_{mm}^{-1} \hat{s}$$

where $\mathfrak{R}_{mm}=MM^T-\sigma^2 \hat{s}\hat{s}^T$

The amplitude of 3 input heartbeat signal is normalized by calculating the variance (or standard deviation) of each channel when the user is not running.

Figure 15:
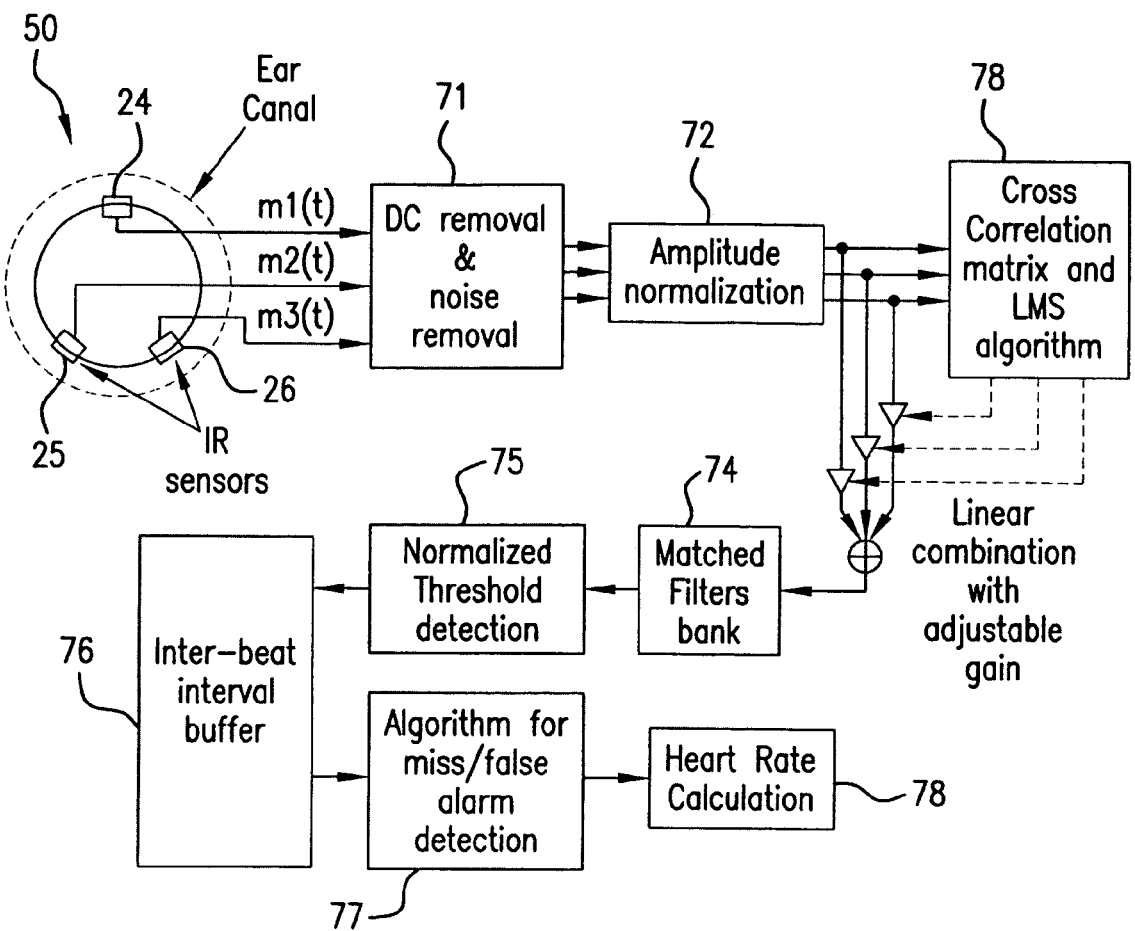
FIG. 15 is a block diagram of a method for detecting steps taken by a user during walking or running.

FIG. 15 schematically illustrates the processing of the sensor signals 31, 32, 33 to determine heartbeat. The following is a description of each block.

Block 71:

A simple Finite Input Response (FIR) low pass filter is used to remove all high frequency signals. Slow drifting DC offset is removed using a filter or a moving window to extract the DC offset and subtract back from the signal.

Block 72:

The signal amplitude of the heartbeat signal on each sensor is identified when there is no user motion. This is done by calculating the standard deviation of the 3 input signals when there is no motion. The 3 signal paths are then normalized.

Block 73:

We then determine whether there is motion. The signal are check in the time domain. If the heartbeat signal dominates, all the 3 signals should be synchronous and in-phase. If the motion of the user is big enough, it is expected that the signal from motion dominates and sensor signals should not be all in phase. The correlation index across the three signals is calculated. The amplitude of the signal when compared with rest time signal amplitude is a clear indicator for motion.

If there is no motion the three signals are added together (with normalized amplitude) to improve the SNR.

If there is motion: e.g. running, the acquired signals are cut into blocks of length K for calculating the covariance matrix $\Re_{mm} = MM^T - \sigma^2 \hat{s}\hat{s}^T$.

$\sigma^2 \hat{s}\hat{s}^T$ can be obtained calculating the standard deviation of the 3 input signals when there is no motion. The 3 input signals are then normalized to having signal standard deviation of $\sigma$ when there is no motion. Then $\sigma^2 \hat{s}\hat{s}^T$ becomes $$\sigma^2 \begin{bmatrix} 1 & 1 & 1 \\ 1 & 1 & 1 \\ 1 & 1 & 1 \end{bmatrix}$$

We then calculate the vector: $w = \Re_{mm}^{-1} \hat{s}$

All 3 channels are calibrated and normalized when there is no motion $\hat{s} = [1 \ 1 \ 1]^T$ w is a 3×1 column vector: $\hat{y} = \hat{w}^T M$ y[n] is a linear combination of the 3 input signals the signal due to motion should be canceled out and preserve the heartbeat signal The linear combination may also be done in frequency domain as well. The time domain waveform can be restored using an inverse Fast Fourier Transform (FFT). The signal y[n] should contain the heartbeat signal+noise.

Block 74

The heartbeat signal is detected using match filters in the time domain. The user's resting heartbeat rate signal can be recorded as templates. The corresponding heart rate of these templates can be calculated and recorded as well. For each range of the heart rate, a template is stored for each user. For the range where there is no recorded template a time wrapping approach is used to predict an approximate template. These templates are then used to build multiple matched filters for the user. The corresponding matched filter will be selected according to current heartbeat rate of the user.

Block 76

The peaks of the matched filter output are detected and they are marked as the beat time. The inter-beat intervals are calculated and stored in a buffer.

Block 77

Based on the current beat rate, an algorithm was implemented to detect missed and false alarm of the beats. In case of a miss or false alarm the inter-beat intervals will be modified accordingly to improve accuracy of the heart rate calculation.

Block 78

The heart rate is then calculated from the inter-beat intervals buffer.

Figure 16:
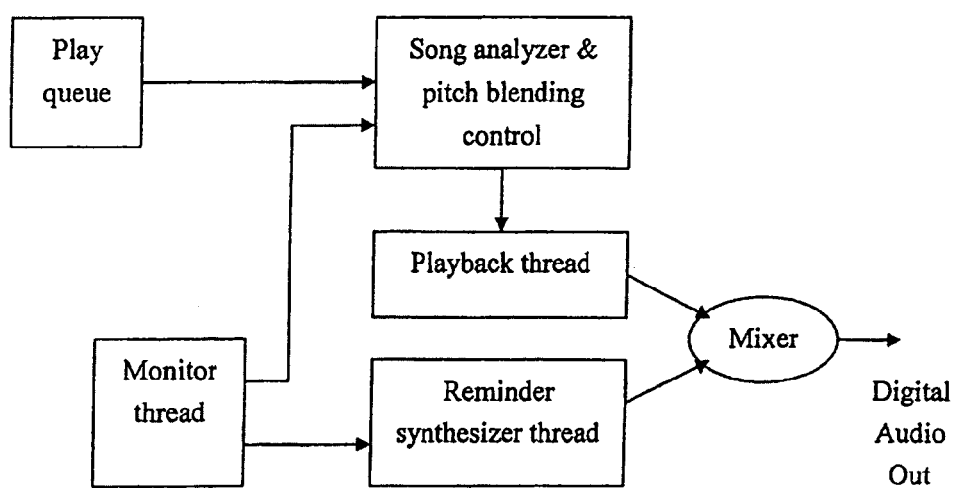
FIG. 16 is a schematic block diagram of body parameter base playback control in the exercise device.
Figure 17:
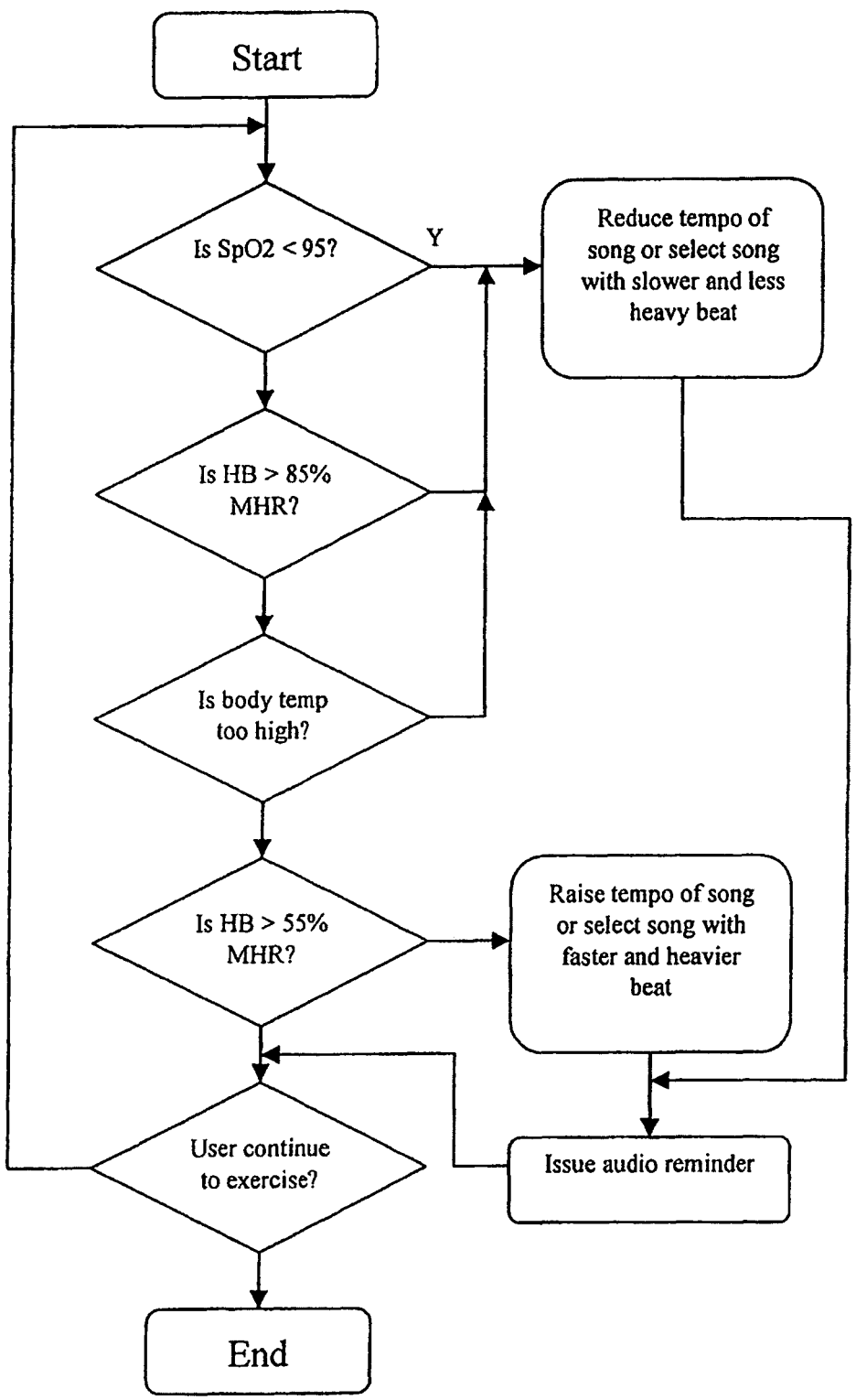
FIG. 17 is a flow chart of the implementation of the body parameter based playback control.

The exercise device processes, displays and stores health related data, such as heart rate, blood oxygen level (SpO2), body temperature, steps walked or run, entered weight to calculate calories burned and body mass index (BMI). The user connects to the headphones that not only playback audio files but also simultaneously captures end users health related data inside the ear. The data is transferred to the portable entertainment device and workout assistant for processing, displaying/notifying and storing the data. The following various functions are available on the device. This is, however, not an exhaustive list and more or less features may be included in some embodiments. Preferred features include;

1. Playback of the audio/video files stored on the device,
2. Determining and displaying the instantaneous heat rate and storing a heat rate profile during an exercise period.
3. Storing and displaying the number of steps taken.
4. Determining, displaying and storing the health related status of the end user, including temperature, blood oxygen level and other body parameters.
5. Providing visual and audio feedback of target exercise parameters and/or rates to help the end user optimize his physical activity—for example a pre approved beep as a sign to slow down, a pre approved different signal/sound for signaling end user to pick up the pace and a pre defined sound for providing signal on what percentage of the exercise has been completed.
6. Transfer of date to a PC for further analysis, review or summary,
7. Providing visual and audio feedback, for example via pause or stop playback, if the device detects one or more of the ear buds is not capturing a heartbeat which mean a possible detach and resume playback after the device detects a heartbeat from one or both of the ear buds.
8. Providing visual and audio feedback of target exercise parameters by changing the tempo, pitch, equalizer according to the inputted vital sign so as to raise or reduce the workout intensity of the user sub-consciously—FIGS. 16 and 17 shows the block diagram of the way to implement the change of audio signal based on vital sign.

The invention claimed is:

1. A method of determining heart rate of a person during exercise comprising:
    positioning a plurality of heart beat sensors at respective locations on a body part of the person, a circular support member circumferentially engaging the body part of the person, the plurality of heat beat sensors including:
       three light emitters spaced at 120° intervals on a circumference of the circular support member emitting light into respective areas of tissue of the body part, and
       a plurality of light detectors on the circumference of the circular support member and respectively detecting the light emitted by the three light emitters that is reflected from the respective areas of tissue of the body part;
    obtaining a plurality of sensor signals from the heart beat sensors, the sensor signals comprising heart beat signals and movement signals,
    comparing the sensor signals to separate the heart beat signals and the movement signals from the sensor signals, and
    determining heart rate from the heart beat signals.

2. The method of claim 1, wherein comparing the sensor signals to separate the heart beat signals and the movement signals comprises comparing the sensor signals to find in-phase and out-of-phase components of the sensor signals.

3. The method of claim 1, wherein comparing the sensor signals to separate the heart beat signals and the movement signals comprises finding a covariance between the sensor signals.

4. The method of claim 1, wherein determining heart rate from the heart beat signals comprises match filtering using match filters.

5. A method of determining heart rate of a person during exercise comprising:
- positioning a plurality of heart beat sensors at respective locations on a body part of the person, a circular support member circumferentially engaging the body part of the person, the circular support member including an audio speaker, the plurality of heart beat sensors including:
  - three light emitters spaced at 120° intervals on a circumference of the circular support member emitting light into respective areas of tissue of the body part, and
  - a plurality of light detectors on the circumference of the circular support member and respectively detecting the light emitted by the three light emitters that is reflected from the respective areas of tissue of the body part;
- obtaining a plurality of sensor signals from the heart bet sensors, the sensor signals comprising heart beat signals and movement signals;
- comparing the sensor signals to separate the heart beat signals and the movement signals from the sensor signals; and
- determining heart rate from the heart beat signals;
- wherein the audio speaker selectively outputs audio content responsive to the heart rate determined from the heart beat signals.

6. The method of claim 5, wherein comparing the sensor signals to separate the heart beat signals and the movement signals comprises comparing the sensor signals to find in-phase and out-of-phase components of the sensor signals.

7. The method of claim 5, wherein comparing the sensor signals to separate the heart beat signals and the movement signals comprises finding a covariance between the sensor signals.

8. The method of claim 5, wherein determining heart rate from the heart beat signals comprises match filtering using match filters.

* * * * *